United States Patent [19]
Tawashi

[11] Patent Number: 5,648,101
[45] Date of Patent: Jul. 15, 1997

[54] DRUG DELIVERY OF NITRIC OXIDE

[76] Inventor: Rashad Tawashi, 66 Hyde Park, Beaconsfield, Quebec, Canada, H9W 5L8

[21] Appl. No.: 338,664

[22] Filed: Nov. 14, 1994

[51] Int. Cl.$^6$ .................. A61K 33/00; A61K 33/26; A61K 9/02; A61K 9/14
[52] U.S. Cl. .................. 424/718; 424/400; 424/449; 424/451; 424/463; 424/464; 424/474; 424/475; 424/484; 424/486; 424/489; 424/490; 424/497; 424/501; 424/648; 424/DIG. 15; 514/929; 514/966; 514/967; 514/968; 514/969
[58] Field of Search .................. 424/718, 400, 424/445–446, 449, 451, 463–464, 474–475, 484–486, 488, 491, 493, 496–502, 648, DIG. 15; 423/405; 514/929, 966, 967, 968, 969; 604/19, 27; 623/12

[56] References Cited

U.S. PATENT DOCUMENTS 5,234,956  8/1993  Lipton .................. 514/724
5,583,101  12/1996  Stamler et al. .................. 514/2

OTHER PUBLICATIONS

Johnson, III. Gerald et al., "Cardioprotective Effects of Acidified Sodium nitrite in myocardial ischemia with reperfusion", The Journal of Pharmacology and Experimental Therapeutics, vol. 252(1), pp. 35–41, 1990.

Cotton, F. Albert et al., Advanced Inorganic Chemistry, 5th ed., John Wiley & Sons, New York, 1988, pp. 321–323.

Biological Abstracts 89(9):96652, 1990; abstracting, Johnson et al., "Cardioprotective effects of acidified sodium nitrite in myocardial ischemia with reperfusion," J. Pharmacol. Exp. Ther., vol. 252(1), 1990, pp. 35–41.

Martindale The Extra Pharmacopoeia, (Reynolds et al. eds.), 13th ed., The Pharmaceutical Press, London, 1993, pp. 1220–1221.

The Merck Index, 10th ed., Merck & Co., Inc., Rahway (NJ), 1983, pp. 330–331.

*Primary Examiner*—John Pak
*Attorney, Agent, or Firm*—Samson B. Leavitt; Michael A. Leavitt

[57] ABSTRACT

A method of delivering NO gas to a desired situs on or in the body of a sentient animal, e.g. humans, comprising combining and causing to react a soluble reducing salt, preferably ferrous sulfate, and a nitrite, preferably sodium nitrite, as reactants in the presence of moisture in situ at or adjacent such situs. Means for such delivery include compositions such as tablets, capsules, ointments, creams, lotions, and sprays containing mixtures of particles or granules of the two reactants, and transdermal patches and osmotic pumps for combining solutions of reactant or reactants in situ.

13 Claims, No Drawings

DRUG DELIVERY OF NITRIC OXIDE

FIELD OF THE INVENTION

This invention relates to the drug delivery of nitric oxide (NO), and more particularly to methods, means and compositions for the in situ production and delivery of NO to a desired situs on or in the body of a sentient animal, especially humans.

BACKGROUND OF THE INVENTION

In December 1992 Science magazine named NO the molecule of the year. In the atmosphere nitric oxide is a noxious chemical but in the biological system in controlled small doses it is extraordinarily beneficial. It helps to maintain blood pressure, dilate blood vessels, help kill foreign invaders in the immune response and is a major biochemical mediator of penile erection and probably a biochemical component of long term memory. These are just a few of the many roles which are just beginning to be discovered and have been documented in the scientific literature in the last 5 years.

NO is synthesized from the amino acid L-arginine by the enzyme NO synthase. The release of NO via this enzyme has other pathological or biological consequences including pathological vasodilation and tissue damage. The formation of NO by this enzyme in vascular endothelial cells opened up what can be considered a new era of biomedical and clinical application research. NO released from the endothelial cells is indistinguishable from EDRF (The endothelial derived relaxation factor) in terms of biological activity, stability and susceptibility to inhibitors and promoters. There is available evidence indicating that the cardiovascular system is in a state of constant active vasodilation depending on the generation of NO. Indeed NO can be considered the endogenous vasodilator. Decreased synthesis of NO may contribute to the origin of conditions such as atherosclerosis and hypertension. Nitro vasodilators that have been clinically used the last 100 years and are still widely used in angina pectoris, congestive heart failure, hypertensive emergencies, pulmonary hypertension, etc. are acting through the formation of NO.

Biochemical experimentation has shown that the nitro vasodilator and NO act by activating the soluble guanylate cyclase and it is widely accepted that this activation and the consequent increase in cyclic GMP (guanosine-5',5'-cyclic phosphoric acid) levels induces a sequence of protein phosphorylation associated with smooth muscle relaxation. Nitrovasodilators also generate NO in non-enzymatic reaction, and this leads to the stimulation of soluble guanylate cyclase. The metabolism of nitroglycerin, for example and other organic nitrates by denitration leads to the formation of nitrites which subsequently undergoes biotransformation to generate vasoactive intermediates such as S-nitroso-thiols and nitric oxide. Direct evidence has been established for nitric oxide formation from GTN (glyceryl trinitrate, nitroglycerin) during incubation with intact bovine pulmonary artery. This transformation has been measured chemically and is dependent on incubation time. Nitric oxide provokes vaso-dilatation, and inhibits platelet aggregation. It is involved in increased cerebral cortical blood flow, following the stimulation of nucleus basalis of Heynert in anasthetized rats. Endogenous NO acts as a mediator of gastric mucosal vaso-dilatation. It does not directly modulate the acid secretory response but makes a substantial contribution to the mucosal vaso-dilatation associated with the stimulation of gastric acid secretion. It also mediates estrogen-induced increases in uterine blood flow. The observed vaso-dilatation can be antagonized by the intra-arterial administration of nitric synthase inhibitor L-nitro arginine methyl ester.

Inhaled NO is a selective pulmonary vaso-dilator that can prevent thromboxane-induced pulmonary hypertension during the heparin protamine reaction and does so without causing systemic vasodilation. In biological media NO is very active in a very small concentration. It reacts with $O_2$ to produce $NO_2$ which then forms $NO_2-$ and $NO_3-$ in neutral aqueous solutions according to the following equations:

$$2NO + O_2 \rightarrow 2NO_2 \qquad \text{I}$$

then $$2NO_2 + H_2O \rightarrow NO_2- + 2H^+ + NO-_3. \qquad \text{II}$$

Neither $NO-_2$ nor $NO-_3$ as their sodium salts cause any reaction to vascular strips at a concentration below 10 uMol. The exact physiological stimuli for the generation of NO are not fully understood but the pulsatile flow and shear stress seem to be the main determinants.

NO has a great potential to be applied and used clinically in the treatment of a variety of diseases and can offer a better substitute for a wide range of commercially available vasoactive drugs. This could be realized only if a suitable delivery system is designed for NO administration. Today these systems do not exist and there is a need for the development of these systems. All of the results that have been generated so far were obtained indirectly either by working with NO synthase inhibitors or by delivering NO as Prodrug (organic nitric oxide donors). The authentic bioactive molecule has never been formulated in a convenient delivery system having the capability of targeting and preserving the integrity of nitric oxide molecule. The development and the optimization of such systems is of paramount significance for the use of NO in therapeutics.

Nitric oxide NO, is a colorless gas with a boiling point of $-151.7°$ C., melting point of $-163°$ C. and density of the liquid of 1.269 at boiling point. The NO molecule contains an odd number of electrons. It is soluble in water, 4.7 parts per 100 parts volume per volume at 20° C. and 1 atmosphere. NO reacts readily with oxygen to form brown ntirogen dioxide. Under physiological conditions, nitric oxide can be interconverted to different redox forms with different distinctive chemistries. These forms are NO, $NO^+$ and $NO^-$. Current research indicates that nitrovasodilators carry out their physiological functions by releasing NO (neutral nitric oxide). It is to be noted that the biological half life of this active molecule depends critically on the concentration of the reactants used and on the initial concentration of nitric oxide formed.

OBJECTS OF THE INVENTION

It is an object of this invention to provide methods for the in situ production and delivery of NO to a desired situs on or in the body of a sentient animal, especially humans. Another object is to formulate the authentic proactive NO molecule in a convenient delivery system having the capability of targeting and preserving the integrity of the NO molecule. A further object of the invention is to provide such a delivery system which is easy to operate, economical, using readily available materials, and with dispatch. Other objects of the invention include the provision of compositions, means and devices for carrying out such methods and systems. Other objects and advantages will appear as the description proceeds.

SUMMARY OF THE INVENTION

In accordance with certain of its preferred aspects, this invention comprises the provision of a composition adapted to release or liberate NO gas at or adjacent a desired situs on or in the body of a sentient animal, especially humans, comprising substantially molecularly equivalent amounts of the preferred ferrous sulfate or equivalent water soluble biocompatible reducing agent or mixture thereof such as ferrous chloride, or cuprous sulfate or chloride or the like, and the preferred sodium nitrite, or equivalent water soluble organic or inorganic nitrite such as generally alkali metal and lower alkanol nitrites including potassium, ethyl, amyl, isoamyl and octyl nitrites, erythritol trinitrite and the like, as reactants productive of NO gas in the presence of moisture.

The invention also comprises methods and means for delivering the compositions of this invention and/or NO gas at or adjacent the desired situs on or in the body of a sentient animal.

The following description of the invention is, for the sake of simplicity, reduction of proliferation of paperwork, excessive expansion of obvious alterations, confusion and the like, concerned with the use of ferrous sulfate and sodium nitrite as the preferred reactants.

DETAILED DESCRIPTION OF THE INVENTION

Bearing in mind the unusual physico-chemical and fundamental properties of the NO molecule, this invention provides a novel technology for the administration of this bioactive gas through the following means:

1) Development of an oral system for gastro-intestinal delivery (tablet and capsule).
2) Development of local enhanced topical delivery system (LETDS) such as ointment, suppository and patch.
3) Metered dose inhaler for pulmonary delivery
4) Development of a system of controlled constant rate delivery of NO using osmotic pumping.

The performance of pure NO generated from these delivery systems for a variety of functional target organs or systems depends on the redox state of this molecule. Being an unstable molecule and having a high chemical activity and short half life (of about 30 seconds), it requires unprecedented precautions in formulation and administration. The charge and neutrality of NO facilitates its diffusibility in aqueous media and across the cell membrane. The present invention establishes with certainty the delivery of NO gas to specific sites or organs or for a specific systemic action and guarantees the control of the thermodynamic and kinetic parameters of this reaction between ferrous sulfate and sodium nitrite in the presence of moisture at the micro and nanomol level.

Ferrous sulfate acts herein not only as a reducing agent but as stabilizer for NO, by delaying the action of hemoglobin as an NO scavenger. Ferrous sulfate used in the reaction and which appears in the different formulations is $FeSO_4, 7H_2O$. It dissolves 1 part in 1.5 parts of water at 15° C. It has a molecular weight of 278. Sodium nitrite (Na NO2) on the other hand, has a molecular weight of 69, and the reaction between one mole of ferrous sulfate and one mole of sodium nitrite gives one mole of nitric oxide, NO. This means that the proportion of ferrous sulphate to sodium nitrite is about 4:1 weight/weight.

Stability of NO is maximized in presence of acid. The following equations describe the chemical reaction in presence of acid and moisture.

$$2FeSO_4 + 2NaNO_2 + C_6H_8O_7\text{(ctiric acid)} + H2O \rightarrow 2NaH\,SO_4 + Fe(OH)_3 + FeC_6H_5O_7 + 2NO \quad \text{III}$$

In absence of acid the following reaction is obtained:

$$3FeSO_4 + 3NaNO_2 + 3H_2O \rightarrow Fe_2(SO_4)_3 + 3NO + Fe(OH)_3 + 3NaOH \quad \text{IV}$$

The present invention encompasses the matter hereafter described and the methods of preparation, for the following fields:

1—Gastroenterology/Endoscopy

Nitric oxide is a potent neurotransmitter mediating the relaxation of sphincter muscles. This will have a significant application in gastroenterology and endoscopy. Nitric oxide tablet, capsule, simple or enteric will deliver NO to specific site without systemic effect. The topical application of NO cream, ointment, suppository or transdermal patch will have a significant application in the treatment of conditions associated with anal fissures, some types of constipation, certain skin conditions and the like.

2—Pulmonary Hypertension

Pulmonary hypertension is a disease of unknown origin, with higher incidence among young women. It is characterized by vasoconstriction and high blood pressure in pulmonary arteries which is controlled or inhibited by the use of NO generated by chemical reaction between ferrous sulfate and sodium nitrite in dry powder inhaler (DPI) or in aerosol form as metered dose inhaler (MDI). The reaction will take place only in the lung where moisture is present. The risks of inhaled NO will be eliminated because an exact dose could be delivered in pulses, and for a short contact time. Moreover the risks of NO oxidation involved in mechanical ventilation using the NO gas is minimized.

3—Nitrovasodilators

In the cardiovascular system the release of NO acts as a general adaptive mechanism where the vascular endothelium responds to changes in its environment and regulates blood flow and blood pressure through an action on the vascular smooth muscle. In addition NO regulates the interaction between the endothelium platelets and probably blood borne cells. A prime advantage of NO over nitrovasodilators like nitroglycerin, sodium nitrite, iso-sorbide dinitrate and penta erythritol tetranitrate, is that the authentic NO drug molecule is directly delivered. The risk of varied response associated with oral and transdermal delivery and the risks of cutaneous metabolism are eliminated. There is less of a chance of over or under dosage with this system in addition to a higher degree of reproducibility and less side effects. Available information indicates that the relation between nitroglycerin plasma concentration and anti-anginal effect has not been well characterized. Experienced investigators raised many questions about the extent of cutaneous metabolism of GTN. Results available indicate clearly that organic nitrates used as vasodilators must undergo biotransformation to NO before vasodilatation can occur and that the mechanism of organic tolerance involves decreased formation of NO. The use of the osmotic pumping technique for the delivery of a constant rate of NO is more effective and safer than the use of intravenously administered sodium nitroprusside. The development of this NO delivery technology enables administration of the exact dose, establish dose response relationship, monitor the hemodynamic activity, and adjust and control the administered dose. NO will act not only as vasodilator but increases the permeability of the blood brain barrier to allow nerve growth factors and other important neurotrophic agents to reach their target cells. Topical NO delivery will be the treatment of choice for Reynaud's phenomenon, where capillary vasoconstriction is the underlying cause.

4—Vaso-Active NO in Male Impotence

The use of vaso-active drugs is increasing in urology clinics worldwide. These drugs have been formulated and introduced for auto-injection. Their action as a single active component or as a mixture is not certain in all patients. The present development of NO delivery by the transdermal or transuretheral route is more effective and will eliminate risks and inconveniences associated with the intracavernous injection of papaverine or PGEI (prostaglandin E1) or their cocktails. The ability of the patient to terminate the medication if needed by removing the transdermal device, in addition to patient acceptance, is an obvious advantage.

For the preparation of granules, 1 part of ferrous sulfate powder, mixed with about 0.25 to 15, preferably about 0.25 to 1.5, parts of a water soluble conventional filler such as xylitol, sorbitol, lactose or the like, and preferably about 0.2 to 0.5 parts of water soluble organic acid, preferably citric acid, is granulated with about 0.1 to 1, preferably 0.2 to 1, part of a water soluble granulating or binding agent, preferably polyvinyl pyrrolidone, in the form of alcoholic solution (e.g. 5–15% conc.), dried at elevated temperatures, e.g. about 40° C. to 70° C. for about 5 to 20 hours, as in a hot air oven and sieved, e.g. through a sieve No. 40 to 60.

The sodium nitrite granules are prepared in the same manner with the same materials except for omission of the organic (citric) acid and with about 0.25 parts of sodium nitrite instead of 1 part of ferrous sulfate and then thoroughly mixed with about equal amounts of the ferrous sulfate granules.

Capsules are prepared simply by charging the mixed granules into hard gelatin capsules. The filled capsules disintegrate in water and liberate NO in about 5 to 15 minutes.

Tablets are prepared by mixing 1 part of the mixed granules with about 0.01 to 0.1 part of a mold lubricant and release (anti-adhesive) agent such as polyethylene glycol (PEG) 6,000 and compressed into tablets which dissolve completely within about 12–15 minutes in water liberating NO as effervescent tablets.

The tablets and the capsules prepared as above are if desired coated enterically in known manner in order to liberate NO in the intestine using illustratively formulation No. 5 below. Coating is carried out in a coating pan. The enteric coated tablets and capsules resist disintegration in artificial gastric juice for 2 hours, but when placed in artificial intestinal juice, they disintegrate within 20 min. Tablets and capsules simple or enteric coating are intended to deliver NO for site specific action in the gastro-intestinal tract.

Examples (formulations) 1–5 below illustrate the procedures and materials for preparing the tablets, capsules and enteric coatings thereof according to this invention.

For topical delivery, ointment, cream, lotion, suppository or transdermal patch systems are used. Except for the transdermal patch system, such topical delivery systems employ ferrous sulfate and sodium nitrite granules prepared as described above. One part of a 1:1 mixture of the two types of reactant granules is incorporated into about 4 to 40 parts of a conventional hydrophilic base or carrier such as one or a mixture of PEG's ranging from 400 to 6,000 M.W., the higher molecular weight PEG's averaging over about 2,200 M.W. being relatively more solid for use in suppositories. Examples (formulations) 6–8 below illustrate procedures and materials for preparing the ointments, creams, lotions and suppositories according to this invention. It will be understood that in general sufficient hydrophilic base of the requisite viscosity is employed to provide the desired degree of consistency, spreadability or solidity in preparing the ointments, creams, lotions and suppositories.

The transdermal patch system is similar to the commercially available nitroglycerin or scopolamine patches applied once or twice weekly. Unlike these TTS (transdermal therapeutic systems), the present system is designed to be applied to the skin to deliver NO for a short period of time not exceeding 1 hour. It is intended to deliver NO to the site where it is applied and not to produce systemic effects. The active surface area is about 1–4 $cm^2$. The total amount of ferrous sulfate per patch is about 0.025–0.050 mM of ferrous sulfate per $cm^2$. This ferrous sulfate is present in a multi-layer macroporous or foraminous gauze or cellulosic matrix. The ferrous sulfate could be present with an equal amount of citric acid. Before applying to the skin, sodium nitrite (concentration of 1M in water) is added to the active area of the patch in a quantity of about 50 to 100 microliter. The amount of sodium nitrite added and the amount of ferrous sulfate on the patch decide the dose of NO produced. The pressure sensitive self adhesive membrane has a backing layer of gas impermeable film, e.g. polyethylene, to prevent the loss of NO.

Examples (formulations) 9 and 10 below further illustrate the procedures and materials for preparing transdermal patches according to this invention.

For delivery of NO by dry power inhalation or aerosol, the ferrous sulfate and sodium nitrite in finely divided form (particles or granules) are deposited on finely divided discrete inert finely divided carrier particles to permit delivery in the form of an airborne, vaporous or gaseous dispersion. For this purpose, the carrier particles should be smaller than about 100 micrometers to as low as about 3–5 micro meters, and the deposited reactants of similar small size or even molecular as deposited for example by precipitation from an aqueous solution thereof. The reactants could be deposited as granules prepared as described above in the preparation of tablets and capsules, but of extremely small size, e.g. passing through a No. 100 sieve. The mixture of granules is deposited on the carrier particles by mixing therewith in reactant:carrier proportions of about 1:1 to 1:10. Carrier particles may be natural or synthetic, organic or inorganic. Preferred are lactose crystals, pollen grains, spores, starch grains (preferably rice), and the like. For delivery as a dry powder, any commercially available inhaler may be used such as the Tribohaler and Spinhaler, for delivering the powder in pulse-dosage amounts. According to another inhalation method, an amount of mixture of reactant granules on carrier particles containing sodium nitrite and ferrous sulfate in a weight ratio of about 1:4 per dose, is charged into a pressurized aerosol container with sufficient propellant, e.g. Propellant (Freon) 12, to provide the desired number of doses or individual sprays. The inhaled reactant carrier granule particles produce NO in situ in the respiratory tract and lungs by contact with body moisture.

Examples (formulations) 11 and 12 illustrate procedures and materials for preparing inhalation means according to the invention.

EXAMPLE A

For the constant rate delivery of NO to a desired situs in the body of a sentient animal, it is preferred to employ the known osmotic pump technology. The osmotic pump itself is a rigid or flexible container in the form of a bag, sleeve, sac, can or the like made with a semipermeable membrane or coating, e.g. cellulose triacetate, permitting passage there through of water into the interior of the container into which material to be administered is charged. (Osmotic pump systems are commercially available for example from the ALZA Corporation, Palo Alto, Calif. The container is connected and opens into tubing, rigid or flexible, of metal, e.g., steel, or plastic, e.g. polyethylene, leading to the desired treatment situs.

Using for example ALZA's osmotic pump model Alzet 2001 (two are required), the first pump is filled with 1M. aqueous ferrous sulfate, if desired with an equivalent amount of citric acid, and the second pump is filled with 1M aqueous sodium nitrite. The two pumps are each connected through tubing to a common cannula catheter, e.g. stainless steel, in which the two aqueous reactant solutions are mixed and production of NO begins. The catheter assembly is connected through tubing to the desired treatment situs in the body of the animal through which tubing NO and mixed reactant solutions are fed to said situs. The capacity of the reservoir of this pump model is 200 microliter, the pumping rate of NO is 1 microliter per hour and the duration of the pumping is 1 week. The delivery of NO is initiated when the filled pumps are implanted in the animal body or placed in aqueous physiological solution (water) outside the body.

Using for example ALZA's pumps model Alzet 2ML4 charged with the same reactant solutions, (the capacity of this model is 2 ml.), the delivery rate of NO is 2.5 microlitres per hour for 4 weeks. The amount, rate and duration of NO delivery is programmed and controlled by proper choice of the pump (capacity, type and thickness of semipermeable membrane, etc.) and the concentration of the reactants. Temperature also affects the rate at which water crosses the semipermeable membrane and enters the osmotic sleeve, pump or container, and consequently the in vitro and in vivo pumping rate of the pumps (which varies directly with the temperature).

The following further examples and formulations are only illustrative of preferred embodiments of this invention and are not to be regarded as limitative. All amounts and proportions set forth herein and in the appended claims are by weight, and temperatures are in degrees C. unless otherwise indicated. In the examples, PVP (polyvinyl pyrrolidone) is employed in the form of a 10% solution in ethanol. The PVP has a MW of about 40,000, K value of 10–18 (intrinsic viscosity) although products of 30,000–150,000 MW or more may be employed.

EXAMPLE (Formulation) 1

Tablet Providing 0.36 mM NO

|  | mg |
| --- | --- |
| ferrous sulfate | 100 |
| citric acid | 30 |
| sodium nitrite | 25 |
| mannitol | 85 |
| polyvinylprrolidone (PVP)* | 5 |
| polyethylene glycol 6000 (PEG) | 5 |
| total weight per tablet | 250 mg. |

*as 10% solution in ethanol

EXAMPLE (Formulation) 2

Tablet 0.036 mM NO

|  | mg. |
| --- | --- |
| ferrous sulfate | 10 |
| citric acid | 3 |
| sodium nitrite | 2.5 |
| mannitol | 38.5 |
| PVP | 1 |
| PEG 6000 | 3 |
| total weight | 58 mg. |

The tablets of Examples 1 and 2 are prepared as follows
1—Ferrous sulfate, citric acid, and half of the mannitol are pulverized and screened from sieve No. 40
2—The powder mix is granulated with half the 10% PVP in ethanol and dried at 60° C. for 12 hours in hot air oven.
3—The dried granules are passed through sieve No. 60
4—Sodium nitrite and the rest of mannitol are granulated the same way with the rest of the 10% PVP in ethanol, and the granules dried at 60° C. for the same period of time, then passed through No. 60 sieve.
5—The first granules and second granules are mixed with PEG 6000 (PEG 6000 acts as lubricant and anti-adhesive) and compressed into tablets.
6—The tablets obtained dissolve completely within 12–15 min. in water liberating NO gas as effervescent tablets.

EXAMPLE (Formulation) 3

Capsule 0.36 mM NO

|  | mg |
| --- | --- |
| ferrous sulfate | 100 |
| citric acid | 30 |
| sodium nitrite | 25 |
| lactose | 72 |
| PVP | 4 |
| total weight | 231 mg |

EXAMPLE (Formulation) 4

Capsule 0.036 mM NO

|  | mg |
| --- | --- |
| ferrous sulfate | 10 |
| citric acid | 3 |
| sodium nitrite | 2.5 |
| lactose | 211.5 |
| PVP | 4 |
| total weight | 231 mg |

The capsules of Examples 3 and 4 are prepared as follows:
1—Ferrous sulfate, citric acid and half of the lactose are pulverized and screened from sieve No. 40
2—The powder mix is granulated with one half the 10% PVP in ethanol and then dried at 60° C. for 12 hours.
3—The dried granules are passed through sieve No. 60
4—sodium nitrite and the rest of lactose are granulated the same way with the rest of the 10% PVP in ethanol and the granules dried at 60° C. for 12 hours and then passed through sieve No. 60

5—The first and second granules are mixed thoroughly and used for the filling of hard gelatin capsules (Size No. 2)

6—The filled gelatin capsules disintegrate in water, and liberate NO in 10 min.

EXAMPLE (Formulation) 5

Enteric Coating

The tablets and capsules of Examples 1–4 are coated enterically with the following formulation in order to liberate NO in the intestine. The enteric coated tablets and capsules resist disintegration in artificial gastric juice for 2 hours, but when placed in artificial intestinal juice they disintegrate in 20 min.

|  | grams. |
|---|---|
| CAP* | 120 |
| propylene glycol | 30 |
| Span** | 10 |
| ethanol | 450 |
| acetone | 1000 |

*Cellulose acetate phthalate film former
**Sorbitan monolaurate wetting agent

EXAMPLE (Formulation) 6

Ointment 0.018 mM Nitric Oxide/g.Ointment

|  | mg |
|---|---|
| ferrous sulfate | 10 |
| citric acid | 3 |
| sodium nitrite | 2.5 |
| lactose | 20 |
| PVP | 1 |
| hydrophilic base* | 1936 |
| total weight | 2000 mg |

*PEG 300:400 in 2:3 ratio

EXAMPLE (Formulation) 7

Ointment 0.18 mM Nitric Oxide/g.Ointment

|  | mg |
|---|---|
| ferrous sulfate | 100 |
| citric acid | 30 |
| sodium nitrite | 25 |
| lactose | 200 |
| PVP | 10 |
| hydrophilic base* | 1635 |
| total weight | 2000 mg |

*As in Example 6

EXAMPLE (Formulation) 8

Suppository

For the delivery of nitric oxide in suppository form, the above formulations of Examples 6 and 7, except for change of the hydrophilic base to PEG 4,000:400 in 2:1 ratio, are shaped into suppositories.

The ointments and suppository of Examples 6–8 are prepared first by granulation as described above for the tablets of Examples 1 and 2 using lactose instead of mannitol and the indicated hydrophilic base mixtures of PEG 4,000 and 400 instead of the PEG 6,000 mold lubricant and anti-adhesive or release agent.

EXAMPLE 9

Transdermal Patch

For the transdermal delivery of NO to a situs on the animal skin, a pressure sensitive patch or laminate of an inert foraminous or porous inert cellulose matrix is impregnated with ferrous sulfate solution in an amount or rate of 0.025 mM/square cm. and covered with an outer water resistant foil web. The patch is activated by treatment with 50 microlitres of sodium nitrite solution in water (1M) and immediately applied to the skin where NO gas is released in situ.

EXAMPLE 10

Transdermal Patch

Example 9 is repeated except that the ferrous sulfate is impregnated in an amount or rate of 0.050 mM/square cm. and the activation is with 100 microlitres of the sodium nitrite solution.

EXAMPLE (Formulation) 11

Dry Powder Inhalation

|  | mg. |
|---|---|
| ferrous sulfate | 10 |
| citric acid | 3 |
| sodium nitrite | 2.5 |
| PVP | 0.4 |
| micronized lactose (10 micrometer av. particle size) | 10.1 |
| Total Weight per dose | 25 mg |

1. Granulate the ferrous sulfate and citric acid with one-half the PVP (0.2 mg), dry at 60° C. for 12 hours in vacuum and pass the granules through No. 100 Sieve.
2. Granulate the sodium nitrite with the remaining PVP, then dry and sieve the same way.
3. Mix the granules from steps 1 and 2 with the lactose. Particle size of the powder mix should not exceed 120 micrometers.

The resulting powder mix is charged into a Turbohaler or Spinhaler and expelled into the respiratory tract and lungs at 25 mg. per dose or spray. Liberation of NO is initiated and released in situ by contact of the powder mix with body moisture.

EXAMPLE (Formulation) 12

Aerosol Metered Dose Inhaler

1. Preparation of 20% Ferrous Sulfate on Pollen.

Add 4,000 mg deproteinized pollen to 10 ml. of a 10% solution of ferrous sulfate in water (1,000 mg), mix 10 minutes, dry slowly under vacuum at 50° C. and mix after drying.

2. Preparation of 10% Sodium Nitrite on Pollen.

Add 4,500 mg. deproteinized pollen to 10 ml. of a 5% solution of sodium nitrite in water (500 mg.), mix 10 minutes, dry slowly under vacuum at 50° C. and mix after drying.

3. Preparation of NO Metered Dose Inhaler

Mix 400 mg. of the ferrous sulfate-loaded pollen from step 1 with 200 mg of the sodium nitrite-loaded pollen from step 2, charge the blend into aerosol cans, then add 10 ml. of Propellant 12 (pressurized filling) to provide 100 doses (1 dose=0.10 ml, 100 doses=10 ml.). One dose or spray contains 0.20 mg. of sodium nitrite and 0.80 mg. of ferrous sulfate. Liberation of NO is initiated and released in situ by contact of the spray with body moisture in the respiratory tract and lungs.

Instead of pollen, rice starch grains or spores can be used.

This invention has been disclosed with respect to preferred embodiments and it will be understood that modifications and variations thereof obvious to those skilled in the art are to be included within the spirit and purview of this application and the scope of the appended claims.

I claim:

1. A method of delivering NO gas to a desired situs on or in the body of a sentient animal comprising combining, and causing to react, substantially molecularly equivalent amounts of ferrous sulfate and an organic or inorganic nitrite as reactants with moisture present at or adjacent said situs.

2. A method according to claim 1 employing sodium nitrite as the nitrite.

3. A method according to claim 2 wherein said reactants are delivered to or adjacent said situs in the form of a mixture of discrete granules of each reactant.

4. A method according to claim 3 wherein said granules are made by granulation in admixture with polyvinyl pyrrolidone and citric acid.

5. A method according to claim 4 wherein said granules are delivered in the form of a tablet or capsule containing multiple discrete ferrous sulfate and sodium nitrite granules.

6. A method according to claim 5 wherein said tablet or capsule carries an enteric coating.

7. A method according to claim 4 wherein said granules are topically delivered in an anhydrous hydrophilic base as an ointment, lotion, cream or suppository.

8. A method according to claim 2 wherein said reactants are delivered to or adjacent said situs in the form of a vaporous or gaseous mixture or dispersion of said reactants in finely divided form supported on discrete inert finely divided solid particles.

9. A method according to claim 8 wherein said solid particles comprise lactose crystals, spores, pollen grains or starch grains.

10. A method according to claim 2 employing an adhesive transdermal patch impregnated with dry particles of ferrous sulfate and wetted with an aqueous solution of organic or inorganic nitrite.

11. A method according to claim 2 employing an adhesive transdermal patch impregnated with dry particles of organic or inorganic nitrite and wetted with an aqueous solution of ferrous sulfate.

12. A method according to claim 2 employing osmotic pump technology wherein a first osmotic pump containing an aqueous solution of ferrous sulfate and a second osmotic pump containing a substantially equimolar aqueous solution of organic or inorganic nitrite are inter-connected by tubing to a common cannula catheter assembly leading to and ending at or adjacent said situs of treatment and constant delivery of the mixture of the aqueous solutions and NO gas through said cannula catheter assembly is initiated by implantation of the pumps in the body of said animal or by immersion of the pumps in an aqueous physiological solution.

13. A method according to claim 2 employing osmotic pump technology wherein a first osmotic pump containing an aqueous solution of organic or inorganic nitrite and a second osmotic pump containing a substantially equimolar aqueous solution of ferrous sulfate are inter-connected by tubing to a common cannula catheter assembly leading to and ending at or adjacent said situs of treatment and constant delivery of the mixture of the aqueous solutions and NO gas through said cannula catheter assembly is initiated by implantation of the pumps in the body of said animal or by immersion of the pumps in an aqueous physiological solution.

* * * * *